(12) United States Patent
Muramatsu et al.

(10) Patent No.: US 7,090,983 B1
(45) Date of Patent: Aug. 15, 2006

(54) METHODS FOR DETECTING EARLY CANCER

(75) Inventors: Takashi Muramatsu, Aichi (JP); Kohji Okamoto, Fukuoka (JP); Shinya Ikematsu, Kanagawa (JP); Munehiro Oda, Kanagawa (JP); Hideshi Kumai, Kanagawa (JP); Sadatoshi Sakuma, Tokyo (JP)

(73) Assignee: Muramatsu, Takashi, Nagoya (JP)

( * ) Notice: Subject to any disclaimer, the term of this patent is extended or adjusted under 35 U.S.C. 154(b) by 0 days.

(21) Appl. No.: 10/070,569

(22) PCT Filed: Sep. 8, 2000

(86) PCT No.: PCT/JP00/06147

§ 371 (c)(1),
(2), (4) Date: Jul. 16, 2002

(87) PCT Pub. No.: WO01/20333

PCT Pub. Date: Mar. 22, 2001

(30) Foreign Application Priority Data

Sep. 10, 1999 (JP) ............................. 11-256678
Dec. 3, 1999 (JP) ............................. 11-345404
Feb. 10, 2000 (JP) ............................. 2000-033168

(51) Int. Cl.
*G01N 33/53* (2006.01)
*G01N 33/567* (2006.01)
*G01N 33/574* (2006.01)
*G01N 33/543* (2006.01)
*C12Q 1/00* (2006.01)

(52) U.S. Cl. ................... 435/7.1; 435/4; 435/7.21; 435/7.23; 435/7.92; 435/7.93; 435/7.94; 436/63; 436/64; 436/86; 530/300; 530/350; 530/385; 530/386; 530/387.1; 530/387.7; 530/388.1

(58) Field of Classification Search ............ 435/4, 435/7.1, 7.21, 7.23, 7.92, 7.94, 7.93; 530/300, 530/350, 385, 386, 387.1, 387.7, 388.1; 436/63, 436/64, 86
See application file for complete search history.

(56) References Cited

FOREIGN PATENT DOCUMENTS

| JP | 6-113898 A | 4/1994 |
| JP | 6-172218 A | 6/1994 |
| WO | WO 00/31541 A | 6/1994 |

OTHER PUBLICATIONS

Ye et al. Expression of midkine in the early stage of carcinogenesis in human colorectal cancer. British Journal of Cancer 79(1); 179-184, Jan. 1999.*
Lederman, et al. A single amino acid substitution in a common african allele of the CD4 molecule ablastes binding of the monoclonal antibody, OKT4. Molecular Immunology 28(11): 1171-1181, 1991.*
Li et al., Beta-endorphin omission analogs: Dissociatian of immunoreactivity from other biological activities. Proc. Natl. Acad. Sci. USA 77(6):3211-3214, Jun. 1980.*
Song et al. The Serum Level of Midkine, A Heparin-binding growth factor, as a tumor marker. Biomedical Research 18(5): 375-381, 1997.*
Nakagaware et al. "Differential Expression of Pleiotrophin and Midkine in Advanced Neuroblastomas" *Cancer Research* 55(8):1792-1797, 1995.
Ye et al. "Expression of midkine in the early stage of carcinogenesis in human colorectal cancer" *British J. Cancer* 79(1):179-184, Jan. 1999.
Aridome, K., J. Tsutsui, S. Takao, K. Kadomatsu, M. Ozawa, T. Aikou, and T. Muramatsu. "Increased midkine gene expression in human gastrointestinal cancers." *Jpn. J. Cancer Res.* Jul., 1995. 86:655-661.
Garver, R.I., D.M. Radford, H. Donis-Keller, M.R. Wick, and P.G. Milner. "Midkine and pleiotrophin expression in normal and malignant breast tissue." *Cancer.* Sep. 1, 1994. 74(5): 1584-1590.
Ikematsu, S., A. Yano, K. Aridome, M. Kikuchi, H. Kumai, H. Nagano, K. Okamoto, M. Oda, S. Sakuma, T. Aikou, H. Muramatsu, K. Kadomatsu, and T. Muramatsu. "Serum midkine levels are increased in patients with various types of carcinomas." *Br. J. Cancer.* 2000. 83(6): 701-706.
Koide, N., H. Hada, T. Shinji, K. Ujike, S. Hirasaki, Y. Yumoto, T. Hanafusa, K. Kadomatsu, H. Muramatsu, T. Muramatsu, and T. Tsuji. "Expression of the midkine gene in human hepatocellular carcinomas." *Hepato-Gastroenterology.* 1999. 46: 3189-3196.
Konishi, N., M. Nakamura, S. Nakaoka, Y. Hiasa, M. Cho, H. Uemura, Y. Hirao, T. Muramatsu, and K. Kadomatsu. "Immunohistochemical analysis of midkine expression in human prostate carcinoma." *Oncology.* 1999. 57: 253-257.
Muramatsu, H., et al. "Enzyme-linked immunoassay for midkine, and its application to evaluation of midkine levels in developing mouse brain and sera from patients with hepatocellular carcinomas." *J. Biochem.* 1996. 119: 1171-1175.
Tsutsui, J., K. Kadomatsu, S. Matsubara, A. Nakagawara, M. Hamanoue, S. Takao, H. Shimazu, Y. Ohi, and T. Muramatsu. "A new family of heparin-binding growth/differentiation factors: increased midkine expression in Wilms' tumor and other human carcinomas," *Cancer Res.* 1993. 53: 1281-1285.
Aridome, K. et al., "Truncated midkine as a marker of diagnosis and detection of nodal metastases in gastrointestinal carcinomas," *British Journal of Cancer* (1998), vol. 78, No. 4, pp. 472-477.
Rha, S.Y. et al., "Comparison of biological phenotypes according to midkine expression in gastric cancer cells and their autocrine activities could be modulated by pentosan polysulfate," *Cancer Letters* (1997), vol. 118, No. 1, pp. 37-46.

* cited by examiner

*Primary Examiner*—Alana M. Harris

(57) ABSTRACT

MK (midkine) was found to rise in the blood or urine of patients with various types of cancers at early stage. Based on this finding, a method for detecting early cancer, comprising the step of measuring MK in blood or urine was completed.

13 Claims, 12 Drawing Sheets

METHODS FOR DETECTING EARLY CANCER

This application is a National Stage Application of International Application Number PCT/JP00/06147, published, pursuant to PCT Article 21(2).

TECHNICAL FIELD

This invention relates to a tumor marker for detecting early cancers.

BACKGROUND ART

The degree of cancer progression or enlargement is described as early cancer, advanced cancer, and terminal cancer. Among them, early cancer is generally considered as "a degree of cancer progression in which the tumor is small, shows few metastases, and can be cured permanently or the cancer can be subdued for a long time through treatment".

Early cancer is basically symptomless. Therefore, symptomless subjects are the targets who are tested when trying to nearly completely detect early cancer. Tests targeting a broad range of symptomless subjects to find patients affected by a particular disease, or to narrow down the subjects to those requiring advanced secondary tests, are generally called screening. Generally, in screening, the number of test subjects is extremely large. In order to test many subjects, the screening should first and foremost be convenient and economical. Although testing for tumor markers is a favorable testing method with little invasion of patients, currently, detection of early cancer by measuring tumor markers is considered impossible.

Midkine (hereinafter, referred to as "MK") is a proliferation and differentiation factor that was discovered as a retinoic acid-responsive gene product, and is a 13-kDa polypeptide rich in basic amino acids and cysteines (Kadomatsu, K. et al.: Biochem. Biophys. Res. Commun., 151: 1312–1318; Tomomura, M. et al.: J. Biol. Chem., 265: 10765–10770, 1990). The fact that the MK level is elevated in various malignant tumors compared to the surrounding normal tissues, suggests that MK plays an important role in carcinogenesis. Consequently, diagnosis of cancer by Northern blotting using MK gene as a probe (Unexamined Published Japanese Patent Application No. (JP-A) Hei 6-113898) and a diagnostic agent for cancer containing anti-MK protein antibody (JP-A Hei 6-172218) have been suggested. However, these published patent applications do not describe nor suggest that MK genes or MK proteins are useful in early cancer detection. Thereafter, Ye et al. have reported that MK expression is elevated in pre-cancerous tissues at adenoma stages of human colorectal cancer (Ye C. et al.: Br. J Cancer., 79: 179–183, 1999). However, there is no description or suggestion in this report regarding early cancer detection.

Therefore, the discovery of tumor markers that may be detected from early cancer conditions and the development of tests for detecting such markers have been anticipated.

DISCLOSURE OF THE INVENTION

An objective of the present invention is to provide a novel polypeptide useful as an early cancer marker. In addition, another objective of the present invention is to provide a method for detecting early cancer using this polypeptide as an index. Furthermore, another objective of the present invention is to provide an external diagnostic agent for early cancer that can detect this polypeptide.

The present inventors found that MK levels detected by anti-MK antibodies in hepatocellular carcinoma patients were significantly enhanced at the early stage of hepatocellular carcinoma, not only in hepatocellular carcinoma tissues, but also in the blood and urine compared to healthy subjects or hepatitis patients. Even in gastric cancer, MK levels in the blood and urine were found to be significantly elevated at the early stage, similar to hepatic cancer. Furthermore, in many types of cancers, such as esophageal, duodenal, colon, bile duct and gallbladder, pancreatic, thyroid, lung, and breast cancers, significant elevation of serum MK levels was observed in their early stages. This indicates that MK has an extremely wide spectrum of specificity that is not seen in well-known tumor markers for detecting unspecified cancers.

According to these findings, the present inventors elucidated the utility of MK as an early cancer marker. Furthermore, a screening diagnosis of early cancer was made possible through the highly sensitive detection of MK levels appearing in the body fluid of patients at an early stage of various cancers using a simple and highly sensitive one-step sandwich method developed by the present inventors that utilizes an enzyme immuno assay (EIA). EIA can be completely automated and is extremely useful as a method for measuring MK that aims at early cancer detection.

That is, the present invention relates to a method for detecting early cancer, or a method for diagnosing early cancer, and a diagnostic agent and kit for these methods as follows:

(1) A method for detecting early cancer, comprising:
  a) measuring midkine, and/or a fragment thereof, in a biological sample, and,
  b) comparing the measured level obtained in step a) to a measured level a healthy subject.

(2) The method according to (1), wherein the early cancer is gastric cancer.

(3) The method according to (2), wherein the gastric cancer is at stage I.

(4) The method according to (1), wherein the early cancer is hepatocellular carcinoma.

(5) The method according to (4), wherein the hepatocellular carcinoma is at stage I.

(6) The method according to (1), wherein the early cancer is lung cancer.

(7) The method according to (6), wherein the lung cancer is at stage I.

(8) The method according to (1), wherein the biological sample is serum or urine.

(9) A use of an antibody recognizing midkine, and/or a fragment thereof, for early cancer detection.

(10) A diagnostic agent for early cancer comprising an antibody that recognizes midkine, and/or a fragment thereof.

(11) A kit for detecting early cancer in a biological sample, wherein the kit (a) comprises a container that holds an antibody that specifically binds to at least one epitope of midkine, and/or a fragment thereof, and (b) determines the presence of midkine, and/or a fragment thereof in the biological sample.

(12) The kit according to (11), wherein the antibody is adsorbed onto a solid.

(13) A method for assessing cancer prognosis, comprising:
   a) measuring midkine, and/or a fragment thereof, in a biological sample, and,
   b) correlating the measured level obtained from step a) to cancer prognosis.

(14) The method according to (13), wherein the cancer is gastric cancer, hepatocellular carcinoma, or lung cancer.

Definitions

Unless stated otherwise, the following terms used in this description have the following meanings.

"Early cancer" refers to tumors confined to the site of development (intramucosal) that have not invaded surrounding tissues, or those that have invaded, but the range of invasion is confined to a local area. Especially, tumors showing no invasion are important detection targets in the present invention since they have been difficult to detect by well-known tumor markers. This definition is applicable to almost all cancers such as those of the skin, oral cavity, respiratory tract, gastrointestinal tract, uterine cervix, ovary, gallbladder, bladder, and such. Early cancer includes stage 0 (carcinoma in situ) and stage I according to the TNM classification. In these cancer stages, there are no intravascular invasions or distant metastases, and local tumor ablation alone will lead to complete recovery.

In the present invention, "tumor marker" is defined as a substance produced by tumor cells or cells reacting to tumor cells, which is found in tissues, body fluids, excrements, and such, that can indicate some feature of the tumor, such as its existence, character, or expansion.

The term "MK" includes a full-length MK protein, and a fragment comprising an amino acid sequence of an arbitrary length having the biological activity of MK. Also included are mutant MK, such as a mutant or truncated MK lacking the N-domain that is expressed cancer-specifically (Kaname T. et al.: Biochem. Biophys. Res. Commun., 219: 256–260, 1996.) Midkine is largely composed of two domains, each of which is compactly held by two or three disulfide bridges. Exon 3, which is deleted in the truncated mRNA, encodes the entire domain located in the N-terminal side and some adjacent amino acids. More specifically, the peptide portion between Asp26 and Gly81 was deleted in the truncated form. Thus, the truncated form has about 55% the size of the intact form (Kaname T et al., supra, at p. 258). MK produced by genetic engineering technology, and chemically synthesized MK are used interchangeably in this description. A DNA sequence encoding the human full-length MK is well known (U.S. Pat. No. 5,461,029). Biological activities of MK not only include the physiological action of MK on cells, but also immunological reactivity with an anti-MK antibody.

"Sensitivity" is the ratio of positive measurements in a tumor-existing group, and is also called positivity ratio.

"Specificity" is the ratio of negative measurements in a tumor-non-existing group, and is also called negativity ratio.

"Biological sample" means a sample that can be obtained from an organism. More specifically, it is, for example, blood, serum, urine, other secretions, and such. Among these biological samples, urine is useful as a sample with low invasiveness. Since urine volume changes considerably, urine volume correction is desirable for a more accurate comparison of urine component concentrations. Creatinine correction and such are well known methods for correcting urine volume.

"Stage classification" is generally, classification of cancer by progression observable by the naked eye, and TNM classification (tumor-node-metastasis staging) is widely used internationally. The "stage classification" used in the present invention corresponds to the TNM classification ("Rinsho, Byori, Genpatsusei Kangan Toriatsukaikiyaku (Clinical and Pathological Codes for Handling Primary Liver Cancer)": 22p. Nihon Kangangaku Kenkyukai (Liver Cancer Study Group of Japan) edition (3rd revised edition), Kanehara Shuppan, 1992).

Furthermore, in the present invention, "detection of cancer" means judging that cancer exists in a subject's body with a high probability. In contrast to detection, screening is a term indicating tests that especially target an arbitrary group, and intends to narrow down subjects with a strong possibility of having a cancer. The detection of cancer targeting a particular subject is called diagnosis, whereas screening targets arbitrary groups. In the present invention, screening and diagnosis differ only in their targets, and the cancer detection method of the present invention comprises both.

Since the levels of markers produced by cancer cells in the blood do not differ from their standard values in a healthy subject until the cancer grows to a certain size, early cancer detection by an increase in the level of a serum marker is normally considered to be impossible, as mentioned above.

Since MK is highly expressed at the mRNA and protein levels in pre-cancerous stages of colorectal cancer (Ye C. et al.: Br. J. Cancer., 79: 179–183, 1999), blood MK levels of patients with various types of cancers were investigated by the present inventors who found that blood MK level was significantly elevated inmost patients (87%) compared to healthy subjects. Eighty-seven percent is an extremely high value compared to existing tumor markers. MK expressed in cancer tissues is probably secreted into the bloodstream, and is thought to lead to an increase in blood MK levels. In hepatocellular carcinoma, gastric cancer, lung cancer, and such, blood MK levels rose in the early stages of cancer.

At stage I, blood MK levels in hepatocellular carcinoma or lung cancer patients were already significantly elevated compared to standard values in blood of healthy subjects, and continued to elevate through stages II to IV. In contrast, in stage I gastric cancer patients, the levels were significantly elevated compared to the standard value in healthy subjects, but from stage II and beyond, regardless of the stage, the MK level remained almost the same. Therefore, this showed that detection of early cancer categorized into stage I is possible through measurement of MK in a wide variety of cancers including hepatocellular carcinoma, lung cancer, or gastric cancer. Furthermore, MK measurement allows detection of not only early cancer, but also cancer at various stages, irrespective of cancer expansion and MK accumulation. This feature is important for tumor markers, because tumor makers found only during early cancer will lead to the risk of overlooking progressed cancer.

The utility of tumor markers are generally evaluated by their "sensitivity" that determines whether a cancer patient is positive, and by their "specificity" that determines whether a non-cancer patient is negative. However, each of the well-known tumor markers has limitations in sensitivity and selectivity.

With MK, its level in blood and urine rises at an early stage compared to the standard level in healthy subjects of various unspecified types of cancers as described in the Examples. This may mean that MK has a wide spectrum of specificity in unspecified types of cancers, and has a high sensitivity. For broad screening of early cancer regardless of the type of organ, high detection sensitivity and specificity towards a specified type of cancer, as well as a wide spectrum of specificity in the detection of unspecified types of cancers are desired. MK is considered to be equipped with such a sensitivity and specificity necessary for screening.

Furthermore, the early cancer detection method based on the present invention augments the limitations in sensitivity and specificity of known tumor markers. It is known that combinations of multiple tumor markers may enable elevation of sensitivity while maintaining invariable specificity. A screening method, that combines multiple tumor markers leading to improved sensitivity and specificity is generally called a combination assay.

In the present invention, early stage detection of the presence of various types of malignant tumors can be detected by measuring MK levels in blood and urine of subjects by EIA and such, through screenings performed on symptomless subjects. Furthermore, sensitivity and specificity may be raised by combining measurements of other tumor markers.

Two points should be considered when performing combination assays. The first point concerns the selection of a tumor marker combination. Once the tumor marker combination is decided, the next consideration concerns how to set its cut-off value.

The essence of tumor marker selection is selecting a combination having the lowest possible correlation to each other. For example, AFP and PIVKA-II, which are liver tumor markers, have a low correlation, and by taking the PIVKA-II cut-off value at 0.1 Au/ml, they exhibit nearly 100% specificity. Meanwhile, the combination of CA19-9 and CA-50, which are pancreatic cancer markers, yields a combination in which true-positive cases are identical, and false-positive cases do not overlap, making it an inefficient combination.

Once a tumor marker combination is selected, the next step is setting the cut-off value. Cut-off value is an important factor influencing sensitivity and specificity. Generally, sensitivity and specificity of tumor markers are in a trade-off relationship, but those skilled in the art can set an appropriate cut-off value following references (for example, Kawamura, T.: Tumor Marker. Nippon Rinsho 54: 1649–1653, 1996).

In an ideal tumor marker, measurements from the tumor group and the non-tumor group do not overlap, and these measurements can determine the presence of tumors. However, such an ideal tumor marker has not been developed so far. Therefore, a cut-off value most appropriate for distinguishing and differentiating tumor groups and non-tumor groups must be set.

In a preferred embodiment, the cut-off value is the mean value of signals obtained when samples from patients without cancer are incubated with solid phase antibodies. Normally, a sample that generates a three-fold signal than the standard deviation of a predetermined cut-off value is considered to be positive for cancer. Often, the upper and lower limits of the 95% confidence interval (standard range) in the distribution of measured levels for healthy subjects are used as the cut-off values. However, standard ranges are set without any consideration of the distribution of the disease state. Therefore, the cut-off values are preferably determined by clearly defining the disease state to be distinguished by the test, then gathering a constant number of a disease group and non-disease group, testing them, and considering the prevalence rate (the situation where testing is applied) and degree of separation (seperability of the test) of the measurements from the two groups. Samples yielding signals with values higher than the cut-off value determined by this method are considered positive for cancer.

Furthermore, blood MK levels significantly decreased in hepatocellular carcinoma patients after surgically removing the tumor. This shows that MK is useful not only for diagnosis of cancer, but also as an indicator for monitoring the course of the disease, as a prognostic factor, or for monitoring relapse. Prognosis means the response of a patient towards a treatment. Therefore, if a decrease in the MK value is measured before and after tumor treatment, and a decrease in the value is confirmed, one can speculate that the treatment being performed is effective. Furthermore, if the measured MK value decreases to that of a healthy subject, one can speculate that tumor treatment has been successful. Tumor treatment includes radiation therapy, immunotherapy, chemotherapy, and such, besides surgical removal.

In another embodiment, MK can be used as a marker for certain types of cancers, such as hepatocellular carcinoma. Blood MK level rises with the advancement of the stage of hepatocellular carcinoma. For cancer diagnosis, the assay described above is performed multiple times sequentially, and the change in MK level is evaluated. For example, this assay is performed over six months to a year, every twenty-four to seventy-two hours, and is performed thereafter as necessary. Generally, cancer is progressing in patients whose MK value, as detected by antibodies, is increasing sequentially.

In the present invention, MK levels within biological samples can be measured by latex agglutination, EIA or RIA method using specific polyclonal or monoclonal antibodies against MK, FIA, chemiluminescence immunoassay, or ECLIA method, and such. Among these, EIA is preferable as an assay for measuring MK in the present invention. Since EIA uses enzymes as labels, EIA can be readily performed compared to RIA that accompanies the problems of half-life and radioactive waste. Further, theoretically, sensitivity of EIA can be enhanced more compared to RIA.

In addition, regarding EIA, various assay systems are known to those skilled in the art (for example, see Harlow and Lane, Antibodies: A Laboratory Manual, Cold Spring Harbor Laboratory, 1988). Particularly, an excellent EIA method has been developed (JP-A Hei 10-160735) for MK measurement, and one skilled in the art can improve this well-known method according to detection purposes as necessary.

In a related embodiment, assays can be performed by using flow-through or strip test type assay in which an antibody is fixed on to a solid membrane such as nitrocellulose. In the flow-through test type, MK in a sample binds to a solid phased antibody as the sample passes through the membrane. Next, when a solution containing a second antibody passes through the membrane, the labeled second antibody binds to the antibody-polypeptide complex. Next, the bound second antibody is detected as described above. In the strip test type, one end of a membrane with a bound antibody is immersed in a solution containing a sample. The sample shifts through the membrane so as to pass through the region containing the second antibody, and then shifts toward the area of the solid phased antibody. Concentration of the second antibody in the solid phased antibody area indicates the presence of cancer. Typically, concentration of the second antibody in that region causes a pattern such as a line that can be read visually. Absence of such a pattern indicates a negative result. Generally, the amount of antibody fixed onto a solid membrane is selected so as to generate a visually distinguishable pattern. In these cases, the MK level in the biological sample is sufficient to cause a positive signal in a two antibody sandwich assay. The amount of an antibody fixed onto a solid membrane ispreferably about 25 ng to 1 μg, and more preferably about 50 ng to 500 ng. Such tests are normally performed with extremely small amounts of biological samples.

In flow-through type or strip test type assay formats, quantitative measurements are possible by automated reading of signal intensities. Alternatively, the sensitivity can be adjusted so that a positive result occurs only when MK is present in a certain concentration or more. Through sensitivity adjustment, positive results can be determined visually without using a special device. The method of adjusting the sensitivity in such types of assay formats is a technology well known to one skilled in the art. For example, sensitivity can be altered by adjusting the amount of antibodies used.

Of course, many other assay protocols are also suitable for use with the antigens or antibodies of the present invention, and thus those described above are only intended to be examples.

MK antibodies necessary for each type of assay protocol described above, and MK used as standard samples are useful as an early cancer detection kit. An early cancer detection kit according to the present invention comprises at least an anti-MK antibody, and MK used as a standard sample. In addition, the detection kit of the present invention can be combined with an enzyme substrate, negative control, and instructions, and such, necessary for the detection of standard components. When detection kits are used in methods such as EIA, the aforementioned anti-MK antibody can be bound to a solid support beforehand. A reaction vessel, beads, or magnetic particles, and such are generally used as the solid phase. By binding anti-MK antibodies to a solid phase in advance, EIA can be not only performed easily, but also automated.

The anti-MK antibody used in the above-mentioned method can be produced by various techniques well known to one skilled in the art (for example, see Harlow and Lane, Antibodies: A Laboratory Manual, Cold Spring Harbor Laboratory, 1988). Anti-MK antibodies may be polyclonal or monoclonal antibodies. For example, monoclonal antibodies specifically recognizing MK, such as those according to Japanese Patent Application No. 2000-272199 (applied on Sep. 7, 2000) by the present applicants may be utilized for the present invention. An antibody fragment containing the antigen-binding site may also be used as an anti-MK antibody. Furthermore, the antibody may be single stranded, chimerized, CDR-grafted, or humanized antibody. The antibody may be produced by the method described herein, or by other methods well known to one skilled in the art.

MK is used as an immunogen for the production of anti-MK antibodies of the present invention, or as standards. MK used for these purposes include biologically derived MK, recombinant MK, or chemosynthetic MK, and furthermore, fragments having biological activity of MK. The method to obtain MK as a recombinant is well known (JP-A Hei 9-95454).

All prior art publications cited in this description are incorporated herein by reference

BEST MODE FOR CARRYING OUT THE INVENTION

Figure 1:
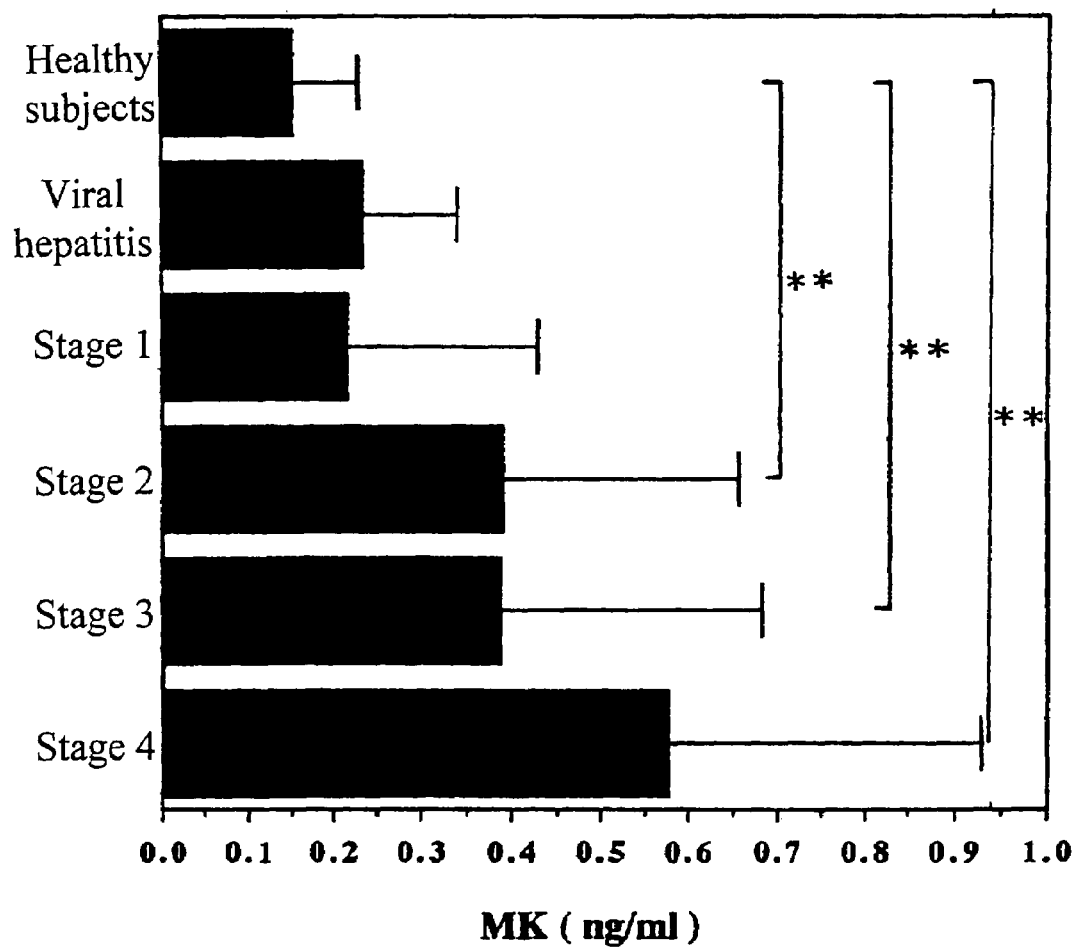
FIG. 1 shows the result of measuring the serum MK level by one-step sandwich method described in (1) of Example 2, in 76 hepatocellular carcinoma patients at stages I to IV (stage I: 7 patients; stage II: 19 patients; stage III: 23 patients, and stage 1V: 27 patients), 7 viral hepatitis patients as a comparative control, and 135 healthy subjects as a control (**$p<0.01$). The error bar indicates standard deviation.

The present invention is specifically illustrated below with reference to Examples, but it is not to be construed as being limited thereto.

EXAMPLE 1

Production of Anti-Human Mk Polyclonal Antibody

MK protein used for immunization and recombinant MK protein used as standard material were produced according to the method described in Example 1 of JP-A Hei 9-95454.

A cDNA covering the ORF of human MK was introduced into pHIL-D4 expression vector having *Pichia* yeast as its host. This MK expression vector was transfected into *Pichia* yeast G115 (*Pichia pastoris* G115; Research Corporation Technologies). An MK expressing clone was obtained by histidine and G418 selection. MK was purified by ion exchange chromatography and affinity chromatography on a heparin column. The neurotrophic activity of purified MK protein was comparable to that of mouse MK produced by recombinant L-cells.

Immunization injections to rabbits and chickens were carried out every two weeks for six times for rabbits, and every two weeks for 8 times for chickens.

Specifically, for rabbits, 400 μg MK containing solution mixed with an equivalent amount of Freund's complete adjuvant was initially injected subcutaneously, and from the second time and onwards, 400 μg MK containing solution mixed with an equivalent amount of Freund's incomplete adjuvant was injected each time subcutaneously. For chickens, the procedure was similar to that of rabbits, except that 100 μg MK was used each time for injections.

Anti-sera obtained from rabbits were precipitated with ammonium sulfate, then IgG was isolated using a protein A column, and furthermore, this was affinity purified using an MK affinity column in which MK has been immobilized onto Affigel-10™ (BioRad), to yield purified rabbit anti-human MK-specific antibodies. On the other hand, anti-sera obtained from chickens were precipitated with ammonium sulfate, and then affinity purified using an MK affinity column to yield purified chicken anti-human MK-specific antibodies. These antibodies were used for detecting human MK specifically in Western blot analysis.

EXAMPLE 2

MK Measurement by One-Step Sandwich Method (1) Rabbit anti-human MK antibodies were dissolved (5.5 μg/ml) in 50 mM PBS (pH7.2) containing 0.1% $NaN_3$, and 50 μl aliquots of this solution were placed into each of the wells of microtiter plates (polysorp plates, Nunc). The plates were maintained at room temperature for 16 hours to adsorb the antibodies onto the wells. After washing with 0.1% Tween 20 in PBS, the wells were blocked by adding 150 μl aliquots of 0.5% bovine serum albumin (BSA) in PBS to each well, and by incubation at 37° C. for 2 hours.

On the other hand, 10 μl each of sera at each stage of liver cancer, sera at each stage of gastric cancer, or sera of healthy subjects (control) were reacted with 100 μl peroxidase-labeled chicken anti-human MK antibodies. (0.1 μg/ml) dissolved with 50 mM Tris-HCl (pH8.4) comprising 0.5M KCl, 0.5% BSA, and 0.01% Microcide I (aMReSCO, Solon, Ohio). 50 μl aliquots of this reaction solution were added into the wells of the plates, and then incubated at room temperature for 1 hour. Each of the wells was washed 5 times with 1% Tween-20 in PBS. 100 μl aliquots of a substrate solution (0.5 mg/ml tetramethylbenzidine) were added into the wells and incubated at room temperature for 30 minutes. The reaction was stopped by adding 2 N $H_2SO_4$, and absorbances at 450 nm/655 nm were measured using a multiplate reader (Model 3550, BioRad). At the time of measurement, a standard curve was made by measuring known concentrations of MK standard by a similar procedure.

(2) Rabbit anti-human MK antibody dissolving buffer was different from that of (1) mentioned above in that, i) 50 mM Tris-HCl (pH8.1–8.3) was used instead of 50 mM PBS, that the buffer contained 0.15 M NaCl, and the antibody concentration was 5 μg/ml; ii) PBS containing 0.1% casein was used as the blocking solution instead of 0.5% BSA; and iii) peroxidase (POD)-labeled chicken anti-human MK antibody dissolving buffer was 50 mM Tris-HCl (pH8.2–8.4) comprising 0.5M KCl, 0.1% casein, 0.5% BSA, 1 mg/ml rabbit γ-globulin, and 0.01% Microcide I (aMReSCO, Solon, Ohio), and otherwise, MK measurements were carried out by the one-step sandwich method in a manner similar to that in (1) mentioned above.

TEST EXAMPLE 1

Correlation Between Each Stage of Hepatocellular Carcinoma and Serum MK Levels (1) Preparation of Serum Samples Blood samples were collected from 135 healthy subjects (94 males and 41 females, between ages 21–75), 76 hepatocellular carcinoma (HCC) patients (stage I: 7 patients; stage II: 19 patients; stage III: 23 patients; and stage 1V: 27 patients), and as liver disease controls, 7 viral hepatitis patients, 72 adenocarcinoma patients (stage 1: 23 patients; stage 2: 9 patients; stage 3: 7-patients; stage 4: 9 patients; stage 5: 5 patients; stage 6: 9 patients; and stage 7: 10 patients), and then sera were prepared therefrom. The Sera were immediately frozen, and were stored at −20° C. until MK measurements.

Thereafter, blood samples were freshly collected from another 376 healthy subjects (152 males and 224 females), and then sera were prepared.

(2) Measurement of Serum MK Levels

Serum MK levels in each HCC patient, viral hepatitis patient, and 135 healthy subjects were measured by the method according to (1) in Example 2 (FIG. 1). The bar in the figure indicates standard deviation. Serum MK levels of HCC patients were confirmed to become significantly higher from stage II compared to those of healthy subjects.

Figure 2:
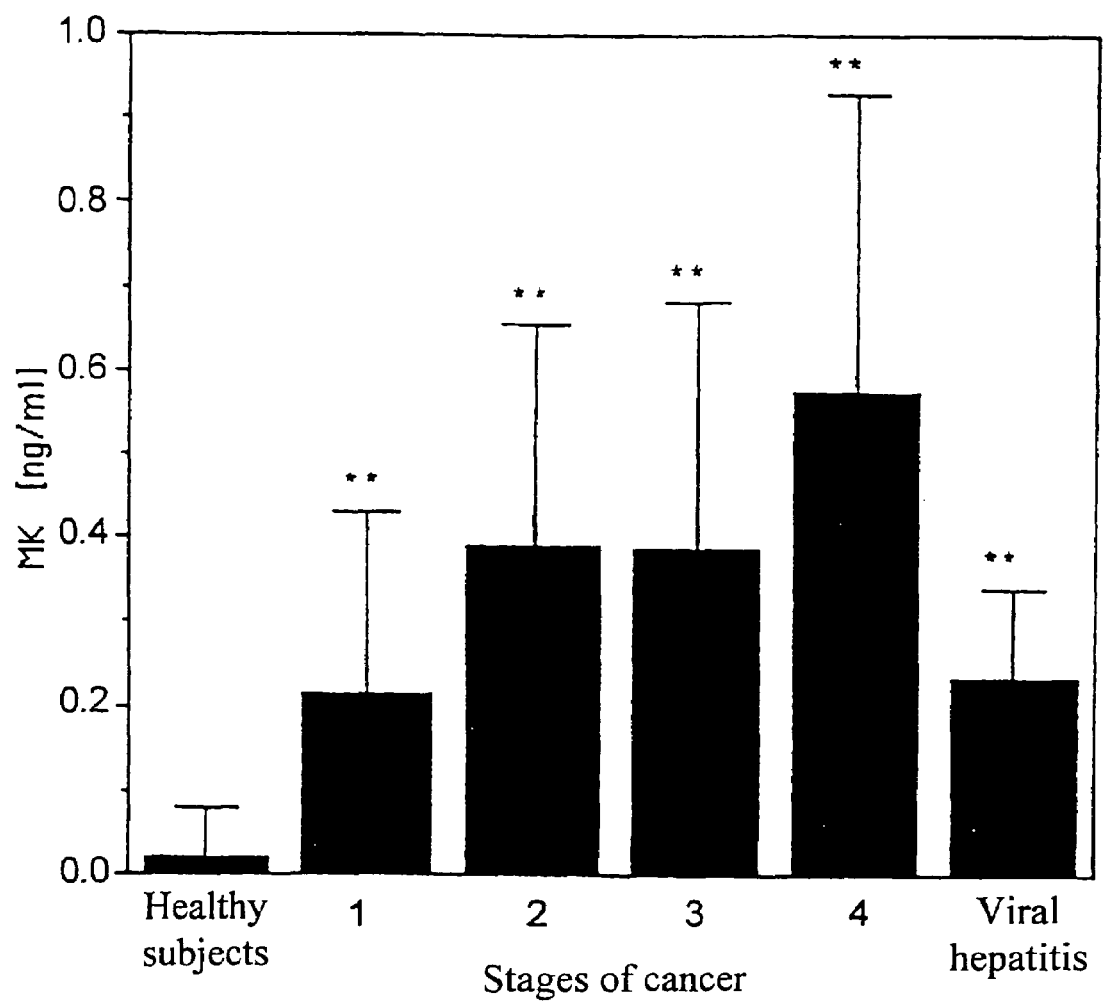
FIG. 2 similarly shows the result of measuring the serum MK level by one-step sandwich method described in (2) of Example 2, in 76 hepatocellular carcinoma patients at stages I to IV, 7 viral hepatitis patients as a comparative control, and 376 healthy subjects as a control (**$p<0.01$, Mann-Whitney U-test). The error bar indicates standard deviation.

Serum MK levels in each of the above-mentioned HCC patients, viral hepatitis patients, and 376 healthy subjects were measured using the one-step sandwich method according to (2) of Example 2, in which sensitivity of EIA was enhanced (FIG. 2). The bar in the figure indicates standard deviation.

Serum MK levels in HCC patients at stage I was 0.22 ng/ml (mean value), a significantly higher value (**$p<0.01$; Mann-Whitney test) compared to 0.02 ng/ml (mean value) obtained for healthy subjects. Therefore, MK was found to be extremely useful as a serum tumor marker for early stage HCC.

TEST EXAMPLE 2

Comparative Test with PIVKA-II and AFP in HCC

Currently PIVKA-II and AFP are used widely as HCC tumor markers. PIVKA-II and AFP are complementary, and combination of PIVKA-II and AFP raises the rate of diagnosis. Therefore, AFP and PIVKA-II were used as comparative control tumor markers.

Figure 3:
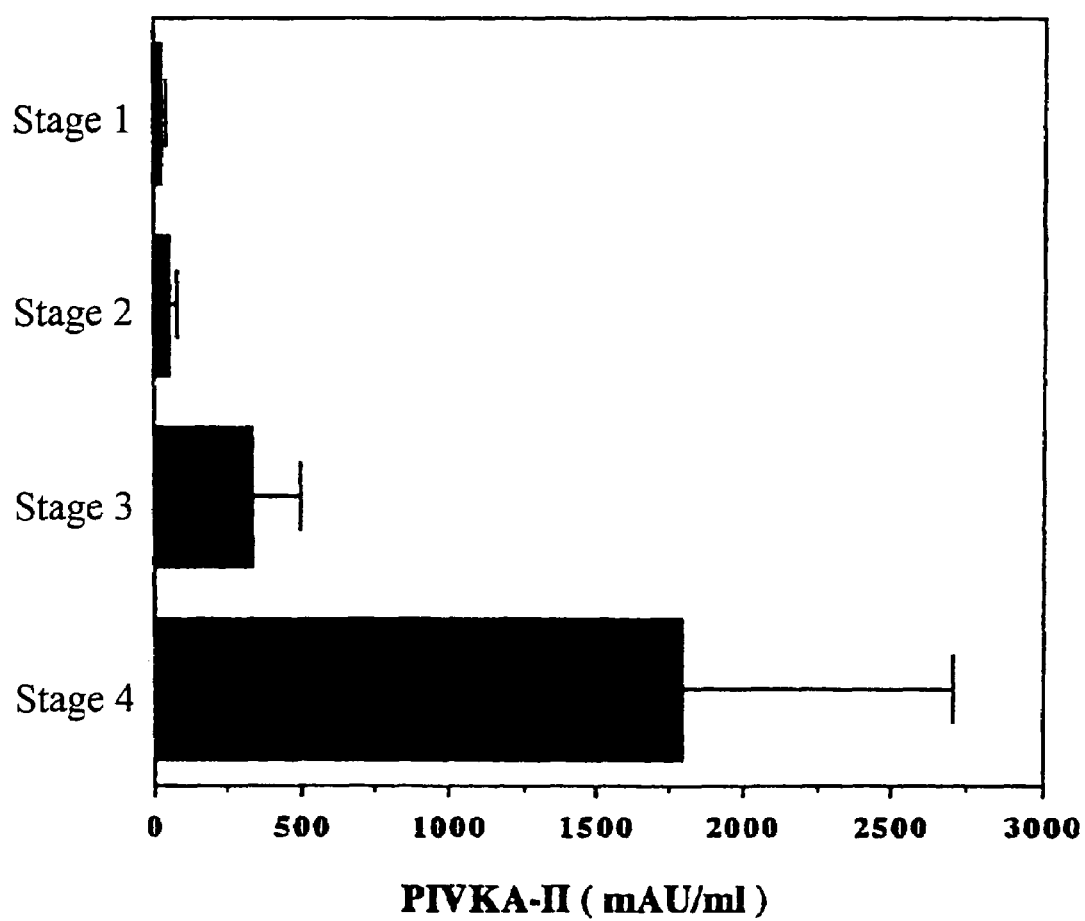
FIG. 3 similarly shows the result of measuring PIVKA-II level in serum of hepatocellular carcinoma patients at stages I to IV, using Eitest PIVKA-II (Sanko Junyaku Co., Ltd.). The error bar indicates standard error.

Serum PIVKA-II was measured using Eitest PIVKA-II (Sanko Junyaku Co., Ltd.) (FIG. 3). The assay was EIA. The possibility that HCC is positive from stage III was suggested.

Figure 4:
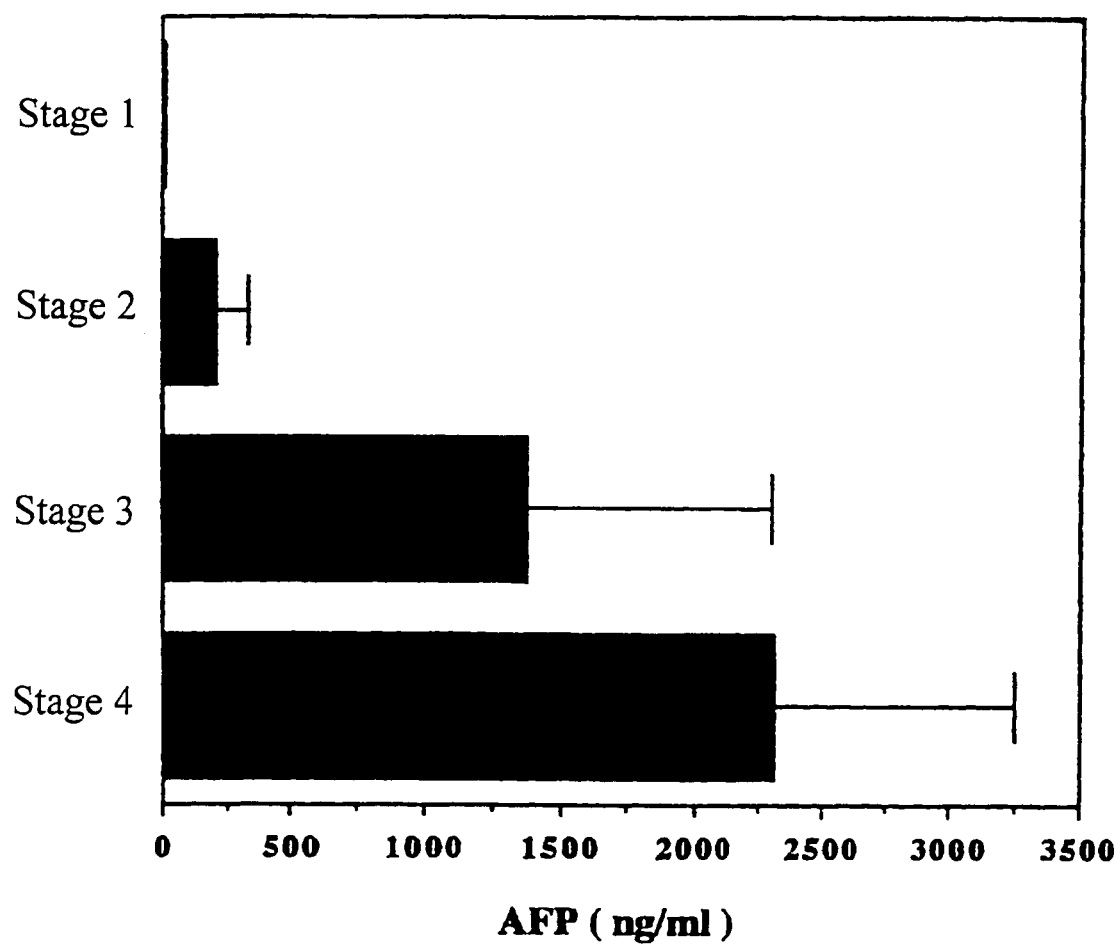
FIG. 4 is similarly shows the result of measuring AFP level in serum of hepatocellular carcinoma patients at stages I to IV, using α-feto RIA beads (Dainabot) (*$p<0.01$). The error bar indicates standard error.

Serum AFP level was measured using α-feto RIA beads (Dainabot) (FIG. 4). The assay was immunoradiometric assay (IRMA). AFP was not detected in HCC at stage I, and detection was suggested to be possible from stage II.

That is, early detection of HCC is possible with MK, furthermore, a strong correlation between HCC stage progression and elevation of serum MK concentration was confirmed.

TEST EXAMPLE 3

Correlation Between Each Stage of Gastric Cancer and Serum MK Levels (1) Preparation of Serum Samples Blood samples were collected from 72 gastric cancer patients (stage 1: 23 patients; stage 2: 9 patients; stage 3: 7 patients; stage 4: 9 patients; stage 5: 5 patients; stage 6: 9 patients; and stage 7: 10 patients), and then sera were prepared. The sera were immediately frozen, and were stored at −20° C. until MK measurement. The values for serum MK levels of 135 healthy subjects and 376 healthy subjects obtained in Test Example 1 were used, individually.

(2) Measurement of Serum MK Levels

Figure 5:
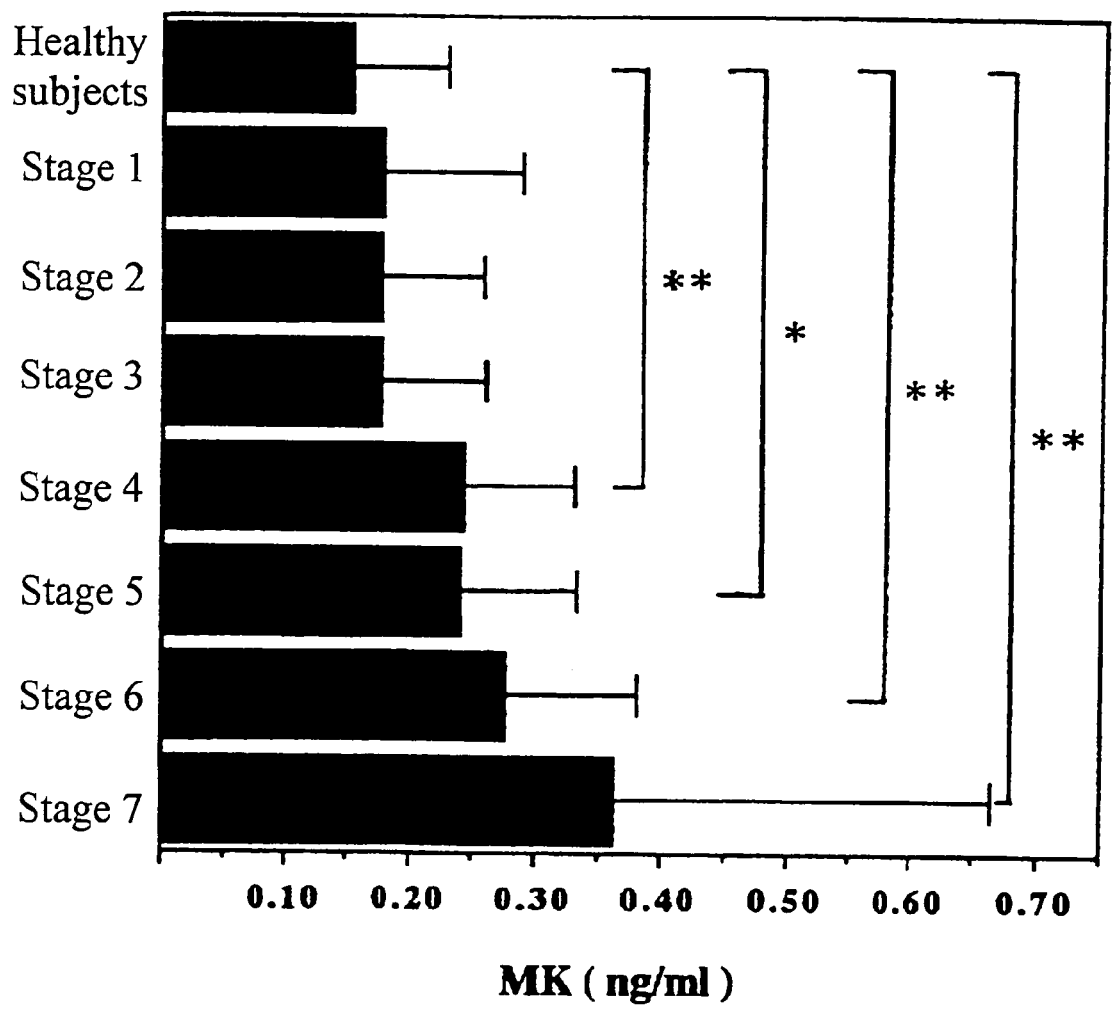
FIG. 5 shows the result of measuring the serum MK level by the one-step sandwich method described in (1) of Example 2, in each of 72 gastric cancer patients at stages 1 to 7, and 135 healthy subjects. The error bar indicates standard deviation.
Figure 6:
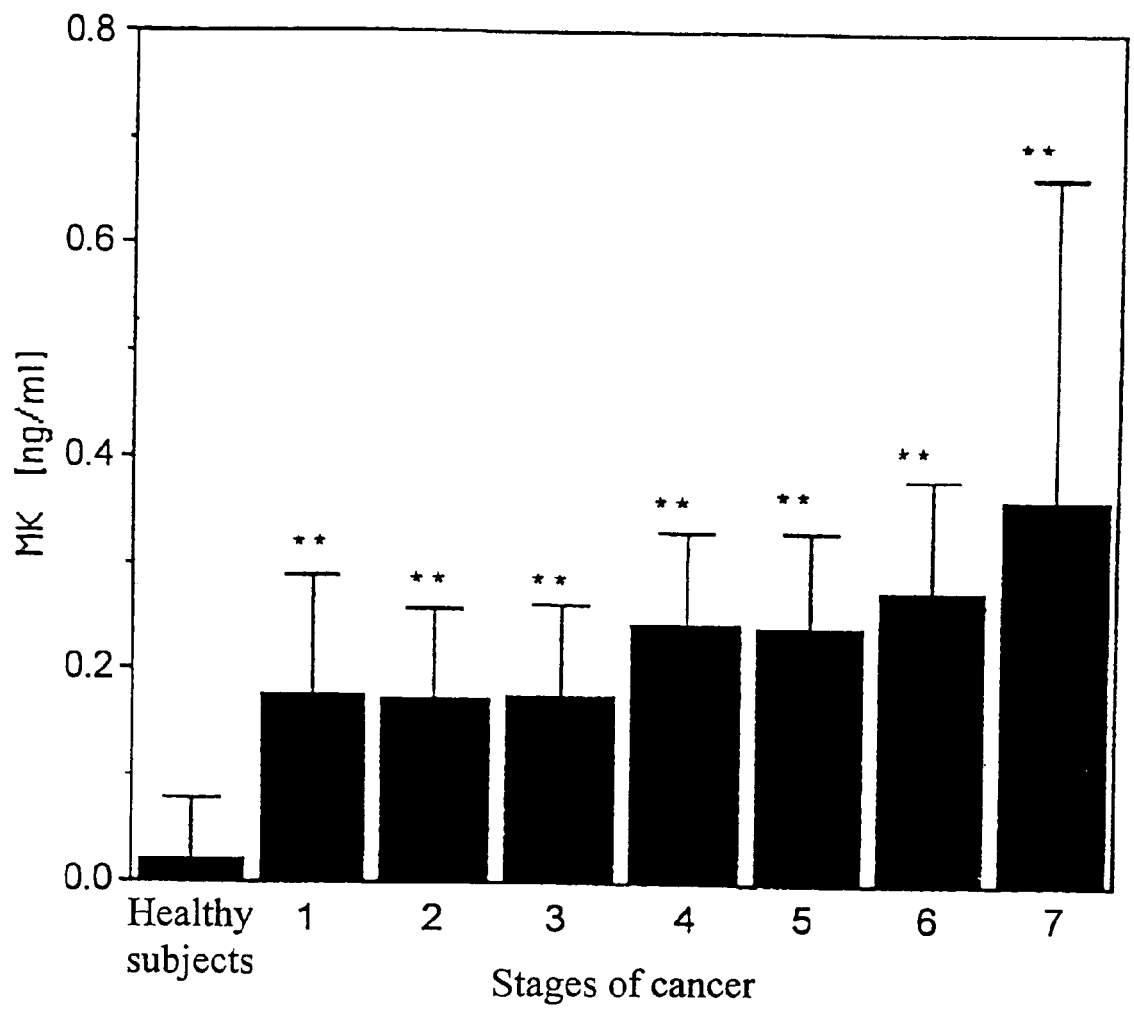
FIG. 6 similarly shows the result of measuring serum MK by the one-step sandwich method described in (2) of Example 2 in 72 gastric cancer patients at stages 1 to 7, and 376 healthy subjects (**$p<0.01$, Mann-Whitney U-test). The error bar indicates standard deviation.

Serum MK levels in each stage (1–7) of gastric cancer and those of 135 healthy subjects are shown in FIG. 5 (the bar in the figure indicates standard deviation), and those of 376 healthy subjects are shown in FIG. 6 (**$p<0.01$; Mann-Whitney U-test; the bar in the graph indicates standard deviation), individually.

FIG. 6 confirmed that serum MK levels in gastric cancer patients are significantly higher than those of healthy subjects from stage 1. That is, MK was found to be useful as a tumor marker for early diagnosis of gastric cancer.

TEST EXAMPLE 4

Comparative Test with CEA and CA19-9 in Gastric Cancer

CEA and CA19-9 were selected as comparative control tumor markers. Serum CEA levels have been found to rise in various cancers of the digestive organs, as well as in various other cancers, and thus are being widely applied clinically. On the other hand, CA19-9 has been found to indicate highly positive values in cancers of pancreas and biliary system. Currently, CA19-9 along with CEA are the most widely used tumor markers for cancers of digestive organs in routine clinical applications.

Figure 7:
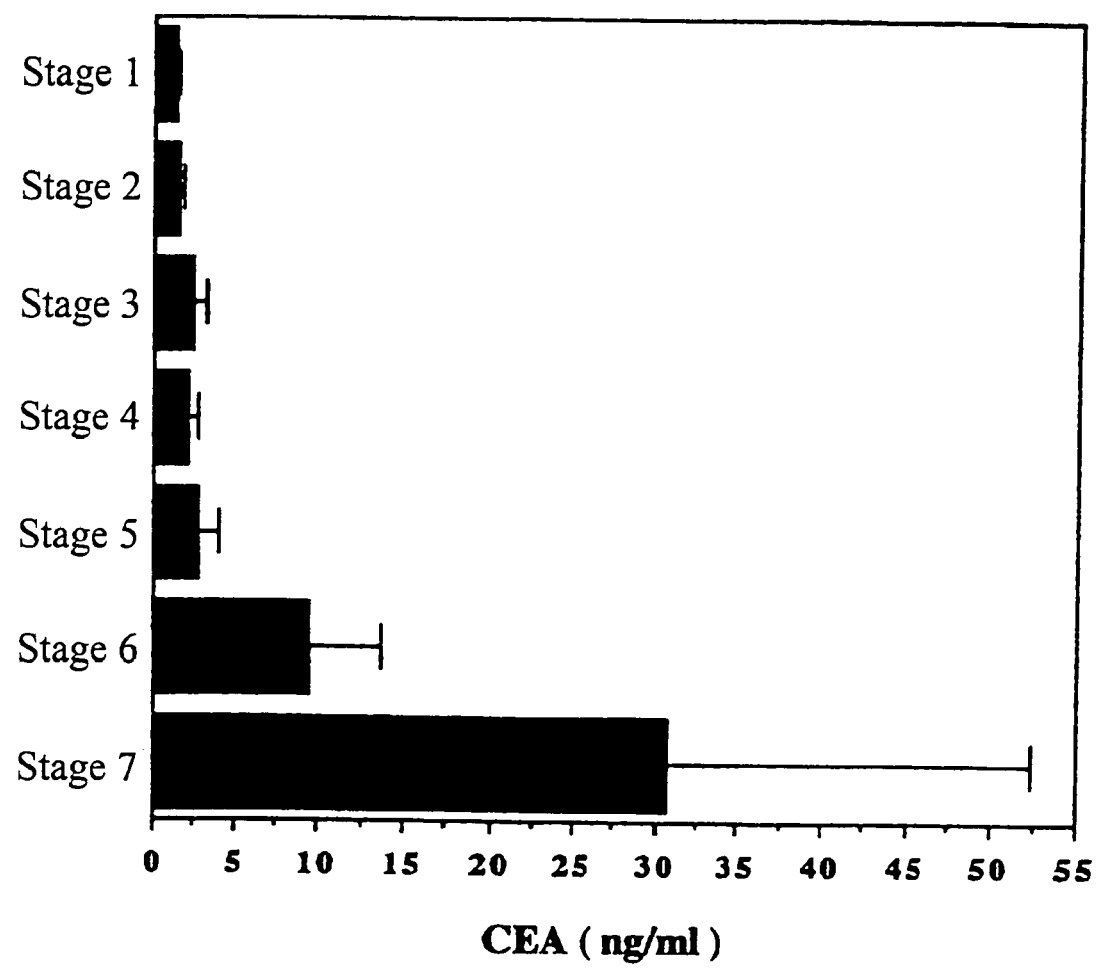
FIG. 7 similarly shows the result of measuring CEA level in the serum of 72 gastric cancer patients at stages 1 to 7 using CEA RIA beads (IRMA method) (Dainabot). The error bar indicates standard error.

Serum MK levels were measured in gastric cancer patients using CEA RIA beads (Dainabot) for serum CEA (FIG. 7; the bar in the figure indicates standard deviation). The assay used was IRMA. Although CEA may be determined as positive from stage 7, significant differences between stages could not be confirmed because of large standard deviations between each of the stages.

Figure 8:
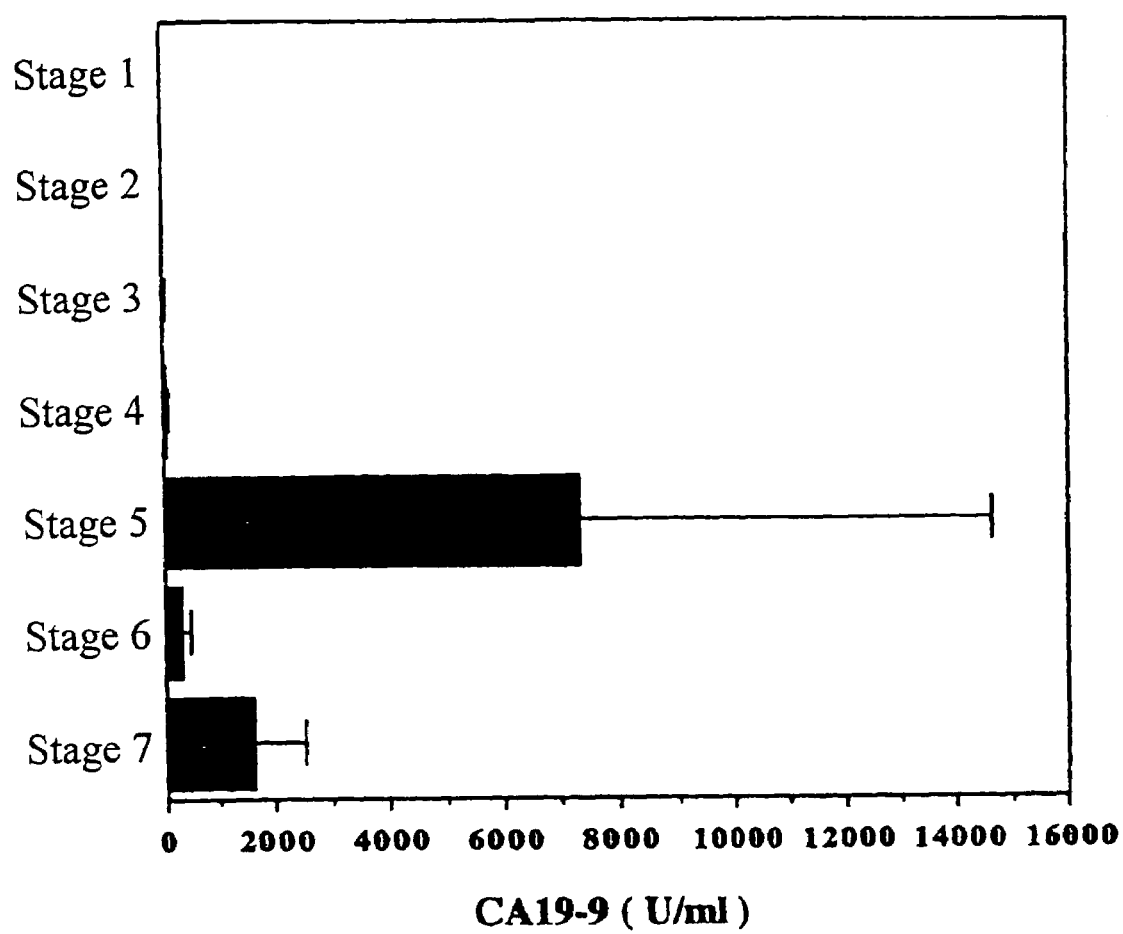
FIG. 8 similarly shows the result of measuring CA19-9 level in serum in 72 gastric cancer patients at stages 1 to 7 using Centocor CA19-9 Kit (IRMA method) (Centocor). The error bar indicates standard error.

Serum CA19-9 was measured using Centocor CA19-9 RIA kit (Centocor; normal value: 37 U/ml or less) (FIG. 8; the bar in the figure indicates standard error). The assay used was IRMA. CA19-9 indicated high values only at stage 5, and is thus speculated to have no correlation to the stages.

That is, MK was found to be useful as a serum tumor marker for early gastric cancer.

TEST EXAMPLE 5

Serum MK Level in Gastric Cancer Patients and Lung Cancer Patients

Serum MK levels were investigated at the early stages in gastric cancer patients and lung cancer patients (Table 1). Both gastric cancer patients and lung cancer patients indicated mean values of serum MK levels at stage I that were lower than those of stages II to IV, but the differences were not statistically significant in both gastric cancer patients and lung cancer patients.

Table 1 Serum MK levels (ng/ml)

| | stage | |
|---|---|---|
| | I | II~IV |
| gastric cancer (n = 31) | 0.73 (n = 18) | 0.93 (n = 13) |
| lung cancer (n = 21) | 1.21 (n = 11) | 2.05 (n = 8) |

TEST EXAMPLE 6

Measurement of Urine MK Levels in Cancer Patients

Figure 9:
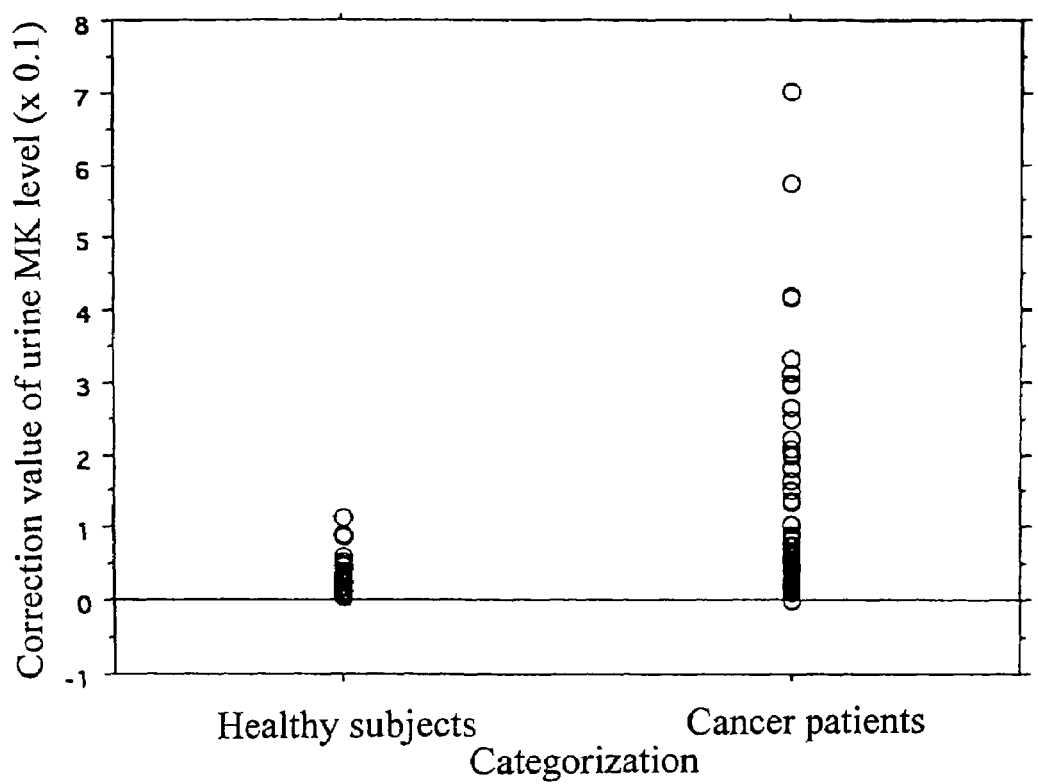
FIG. 9 shows the distribution of urine MK level, which were corrected by creatinine values, in 72 cancer patients (gastric cancer: 24 patients; hepatocellular carcinoma: 24 patients; and colon cancer: 24 patients), and 50 healthy subjects ($p<0.01$; statistics software: StatView-J5.0; using Mann-Whitney U-test).

MK levels of 72 urine samples of cancer patients (gastric cancer: 24 patients; hepatocellular carcinoma: 24 patients; and colon cancer: 24 patients), and 50 morning urine samples of of healthy subjects taken during health checks were measured by the method in (2) of Example 2. Furthermore, creatinine values were measured in the same urine, and then MK values were corrected with the creatinine values. The results are indicated in FIG. 9. A significant difference ($p<0.01$; using Mann-Whitney U-test) was confirmed between urine MK values of healthy subjects and cancer patients.

TEST EXAMPLE 7

Correlation Between Urine MK Values in Cancer Patients and Cancer Stages

Figure 10:
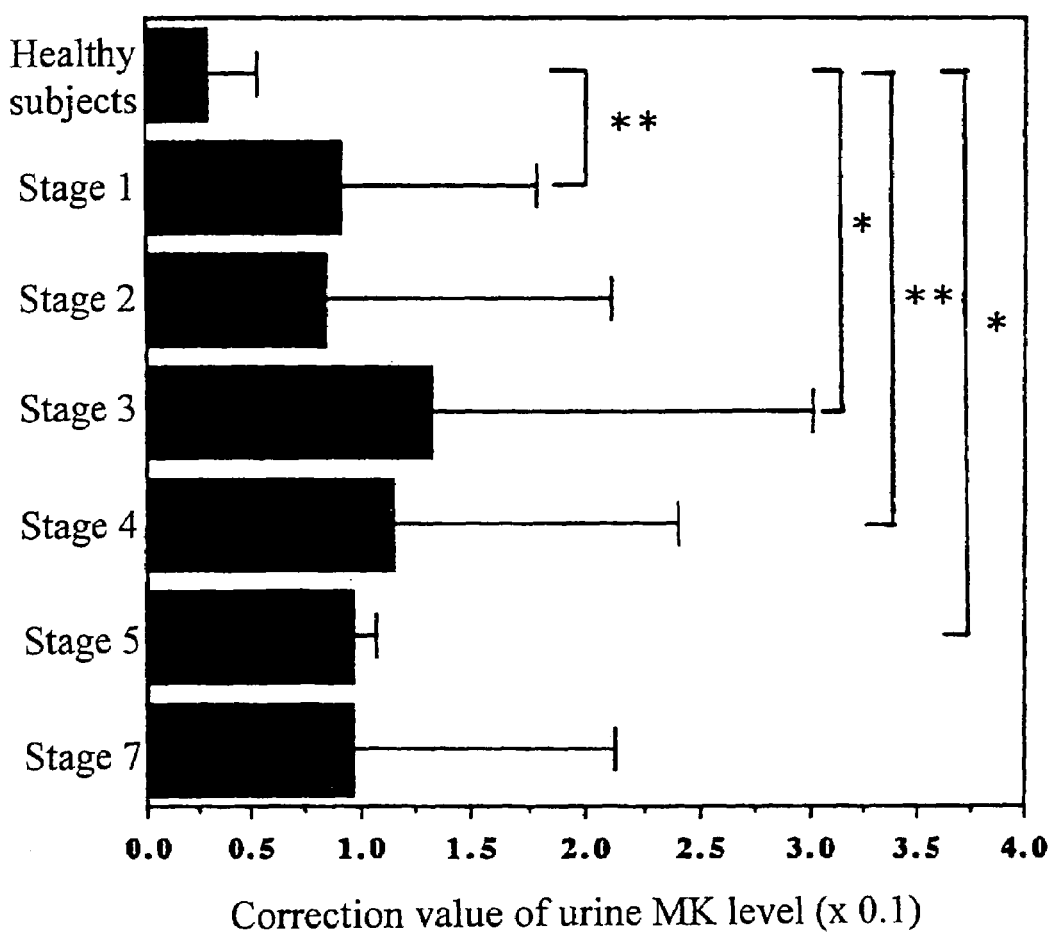
FIG. 10 shows the result of urine MK levels, which were corrected by creatinine values, at stages 1–7 in 3 bile duct cancer, 3 breast cancer, 6 colon cancer, 3 esophageal cancer, 1 gallbladder cancer, 10 hepatocellular carcinoma, 3 pancreatic cancer, 7 rectal cancer, 28 gastric cancer and 1 thyroid cancer patients, 65 patients in total (*$p<0.05$, **$p<0.001$). The error bar indicates standard deviation.

The correlation between urine MK values in cancer patients and cancer stages was investigated. Stage categorizations (stages 1–7) were made on a total of 65 patients comprising 3 bile duct cancer patients, 3 breast cancer patients, 6 colon cancer patients, 3 esophageal cancer patients, 1 gallbladder cancer patient, 10 hepatocellular carcinoma patients, 3 pancreatic cancer patients, 7 rectal cancer patients, 28 gastric cancer patients, and 1 thyroid cancer patient. Then, urine MK levels were measured. MK levels at each stage are shown in FIG. 10 as corrected values of urine MK (*p<0.05, **p<0.01; Mann-Whitney U-test). Urine MK levels were found to rise significantly in stage I of cancer compared to healthy subjects. To date, tumor markers in urine that increase during the early stages of cancer have not been reported. That is, urine MK level is useful for early screening of various cancers.

TEST EXAMPLE 8

Effect of Tumor Ablation on Serum MK Level in HCC

Figure 11:
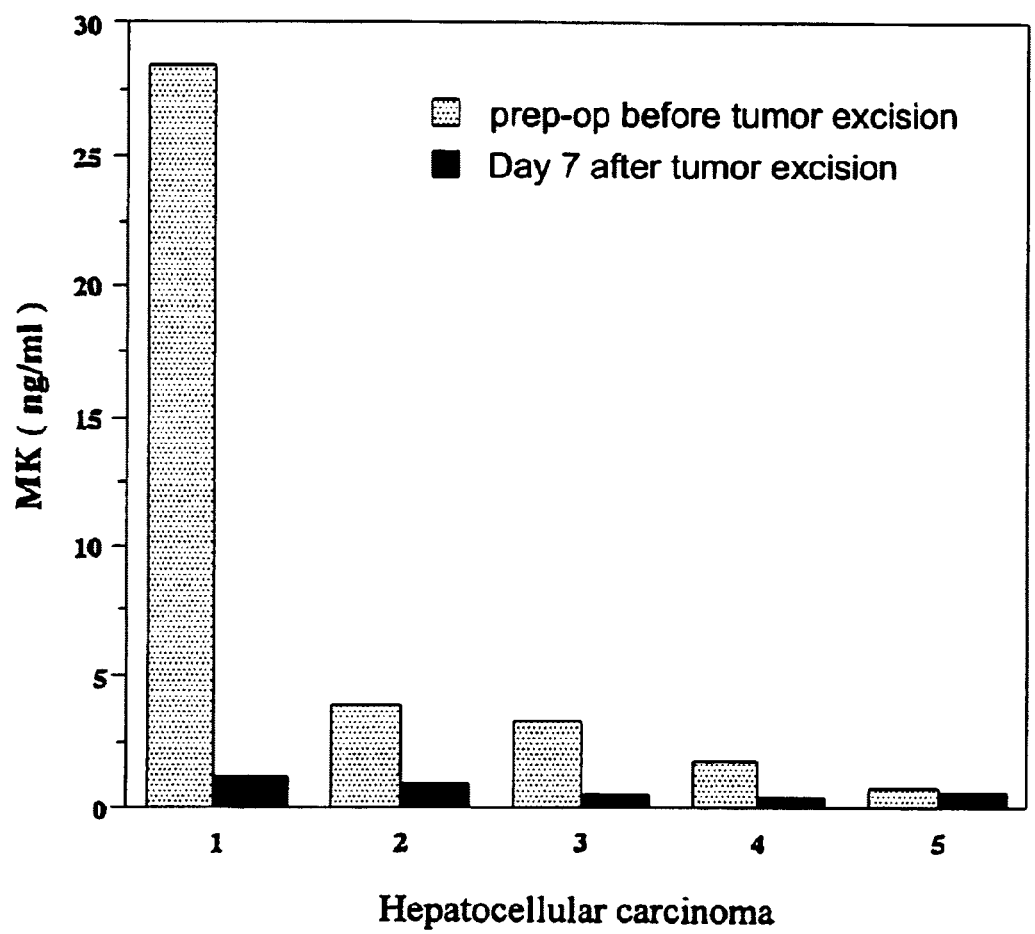
FIG. 11 shows the effect of hepatocellular carcinoma ablation on MK values in serum. The bar containing dots indicates the value before tumor excision (pre-op), and the solid black bar indicates the value after tumor excision (Day 7).

The effect of tumor ablation by a surgical operation on serum MK level was investigated for 5 HCC patients (FIG. 11). In 4 patients, serum MK level significantly decreased 7 days after tumor ablation. That is, serum MK level reflects the therapeutic effect on HCC.

TEST EXAMPLE 9

Serum MK Level in Various Cancers

Figure 12:
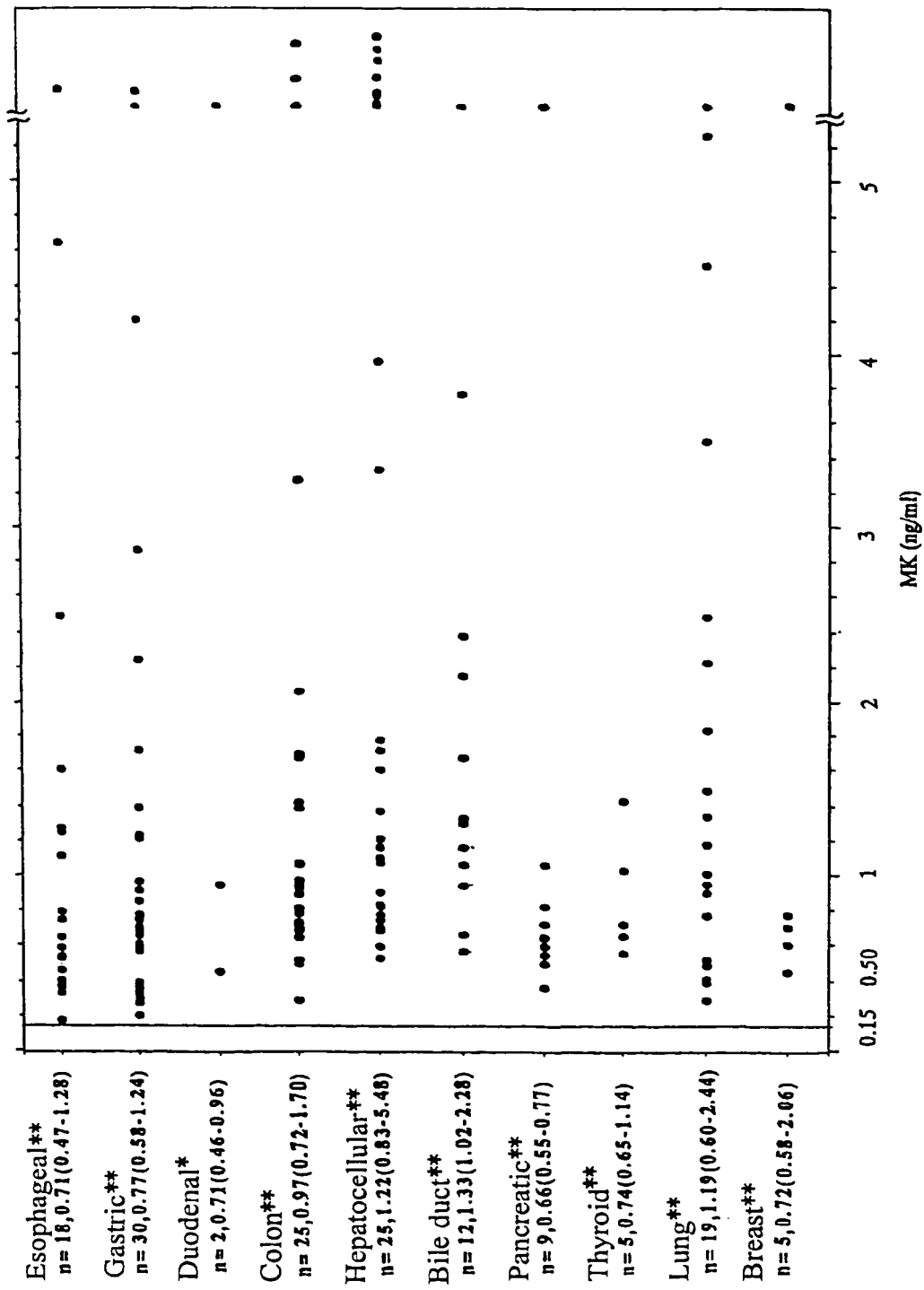
FIG. 12 compares the MK levels in the serum of various types of cancer patients. The thick line indicates the mean value of MK, levels in serum of 135 healthy subjects, and the dotted line indicates 0.50 ng/ml cut-off value. The numbers shown below the names of each type of cancer indicate the number of patients, median value, and the 25% to 75% confidence interval. Asterisks indicate a significant difference (Mann-Whitney U-test) compared to a healthy subject. *: $p<0.05$, **: $p<0.01$

Table 2 itemizes the stages of a total of 150 cancer patients comprising 18 esophageal cancer patients, 30 gastric cancer patients, 2 duodenal cancer patients, 25 colorectal cancer patients, 25 hepatocellular carcinoma patients, 12 bile duct cancer and gallbladder cancer patients, 9 pancreatic cancer patients, 5 thyroid cancer patients, 19 lung cancer patients, and 5 breast cancer patients. The result of measuring the serum MK levels of these 150 cancer patients by EIA is indicated in FIG. 12. Serum MK levels of 150 cancer patients indicated significant difference to those of healthy subjects (p<0.001, Mann-Whitney U-test). Serum MK levels larger than the 0.5 ng/ml cut-off value was seen in 87% of the patients.

TABLE 2

|  | 0 | I | II | III | IV | relapse |
|---|---|---|---|---|---|---|
| esophageal cancer |  | 5 | 4 | 6 | 2 |  |
| gastric cancer |  | 18 | 2 | 6 | 4 |  |
| duodenal cancer |  | 0 | 0 | 2 | 0 |  |
| colon cancer | 1 | 4 | 4 | 5 | 5 | 6 |
| hepatocellular carcinoma |  | 0 | 11 | 9 | 2 | 3 |
| bile duct and gallbladder cancer |  | 2 | 4 | 4 | 2 |  |
| pancreatic cancer |  | 5 | 0 | 1 | 3 |  |
| thyroid cancer |  | 0 | 4 | 1 | 0 |  |
| lung cancer |  | 11 | 1 | 6 | 1 |  |
| breast cancer | 0 |  | 3 | 0 | 1 |  |

INDUSTRIAL APPLICABILITY

This invention provides a tumor marker useful for diagnosing early cancer. The tumor marker is useful for screening early cancer, estimating the stage and prognosis of certain types of cancers, and for monitoring the course of treatment.

The invention claimed is:

1. A method of screening for early cancer, comprising the steps of:
   (a) measuring the level of full-length human midkine, or a fragment thereof, in a body fluid;
   (b) comparing the measured level obtained in (a) to a control human midkine protein level of a healthy subject; and
   (c) diagnosing the presence of early cancer, defined as stage 0 or stage I of the TNM classification, when the comparison of (b) indicates that the measured level is elevated as compared to the control level.

2. The method according to claim 1, wherein the early cancer is gastric cancer.

3. The method according to claim 2, wherein the gastric cancer is at stage I.

4. The method according to claim 1, wherein the early cancer is hepatocellular carcinoma.

5. The method according to claim 4, wherein the hepatocellular carcinoma is at stage I.

6. The method according to claim 1, wherein the early cancer is lung cancer.

7. The method according to claim 6, wherein the lung cancer is at stage I.

8. The method according to claim 1, wherein the body fluid is serum or urine.

9. A method of screening for early cancer comprising the steps of:
   (a) contacting a body fluid with a pair of antibodies that specifically bind to full-length human midkine, or a fragment thereof, in a body fluid;
   (b) comparing the level of binding between the antibodies and human midkine of (a) to a control binding level of a healthy subject; and
   (c) diagnosing the presence of early cancer, defined as stage 0 or stage I of the TNM classification, when the comparison of (b) indicates that the measured level is elevated as compared to the control level.

10. A method for assessing cancer prognosis, comprising the steps of:
    (a) measuring the level of full-length human midkine, or a fragment thereof, in a body fluid both before and after tumor treatment, comparing the level measured after treatment to a level measured before treatment, and
    (b) correlating a difference in the measured levels to cancer prognosis, wherein a reduction in the measured level after treatment is indicative of successful treatment and positive prognosis.

11. The method according to claim 10, wherein the cancer is gastric cancer, hepatocellular carcinoma, or lung cancer.

12. The method according to claim 1, wherein human midkine levels are measured using a sandwich enzyme immunoassay that includes an avian anti-human midkine antibody.

13. The method according to claim 10, wherein human midkine levels are measured using a sandwich enzyme immunoassay that includes an avian anti-human midkine antibody.

* * * * *

UNITED STATES PATENT AND TRADEMARK OFFICE
CERTIFICATE OF CORRECTION

PATENT NO.         : 7,090,983 B1                                         Page 1 of 1
APPLICATION NO. : 10/070569
DATED              : August 15, 2006
INVENTOR(S)       : Takashi Muramatsu et al.

It is certified that error appears in the above-identified patent and that said Letters Patent is hereby corrected as shown below:

Title page of patent, second column
"Primary Examiner—Alana M. Harris" should read   -- Primary Examiner—Alana M. Harris
(74) Attorney, Agent or Firm—Saliwanchik, Lloyd & Saliwanchik--.

Signed and Sealed this

Second Day of January, 2007

JON W. DUDAS
*Director of the United States Patent and Trademark Office*